United States Patent
Høyer et al.

(10) Patent No.: US 9,072,912 B2
(45) Date of Patent: Jul. 7, 2015

(54) SYSTEM FOR ELECTRICAL STIMULATION OF NERVES

(75) Inventors: Michael Høyer, Aalborg (DK); Clemens Florian Eder, London (GB); Morten Hansen, Storvorde (DK); Rune Pank Kristensen, Brønderslev (DK)

(73) Assignee: NEURODAN A/S, Aalborg SV (DK)

( * ) Notice: Subject to any disclaimer, the term of this patent is extended or adjusted under 35 U.S.C. 154(b) by 0 days.

(21) Appl. No.: 13/995,808

(22) PCT Filed: Dec. 21, 2011

(86) PCT No.: PCT/DK2011/000153
§ 371 (c)(1),
(2), (4) Date: Sep. 5, 2013

(87) PCT Pub. No.: WO2012/083952
PCT Pub. Date: Jun. 28, 2012

(65) Prior Publication Data
US 2013/0338734 A1 Dec. 19, 2013

(30) Foreign Application Priority Data
Dec. 21, 2010 (DK) .................................. 2010 01169

(51) Int. Cl.
*A61N 1/00* (2006.01)
*A61N 1/378* (2006.01)
*A61N 1/36* (2006.01)
(52) U.S. Cl.
CPC ............ *A61N 1/378* (2013.01); *A61N 1/36003* (2013.01); *A61N 1/3787* (2013.01)
(58) Field of Classification Search
CPC ........... A61N 1/37211; A61N 1/37229; A61N 1/378; A61N 1/3787

USPC .............................. 607/60, 61, 48, 49, 32, 33
See application file for complete search history.

(56) References Cited

U.S. PATENT DOCUMENTS

| 5,550,452 A | 8/1996 | Shirai et al. |
| 6,331,744 B1* | 12/2001 | Chen et al. .................... 310/171 |
| 7,225,032 B2* | 5/2007 | Schmeling et al. ............. 607/61 |
| 7,403,821 B2 | 7/2008 | Haugland et al. |
| 7,574,262 B2* | 8/2009 | Haugland et al. ............... 607/49 |
| 2008/0228243 A1* | 9/2008 | Maltan et al. ................... 607/57 |

FOREIGN PATENT DOCUMENTS

| GB | 2094574 A | 9/1982 |
| WO | 01/60445 A2 | 8/2001 |

OTHER PUBLICATIONS

PCT International Search Report for International Patent Application No. PCt/DK2011/000153 mailed Mar. 14, 2012.

* cited by examiner

*Primary Examiner* — Michael Kahelin
*Assistant Examiner* — Mallika D Fairchild
(74) *Attorney, Agent, or Firm* — Holland & Hart (57) ABSTRACT

A system for treatment of gait disorders includes an external device in the form of a pulse generator (4) with an integrated rechargeable battery and a device adapted to be implanted in the human body. The system features an external to the body placed antenna (3) for the inductive link between the external device and the implanted device. This antenna further incorporates an additional secondary coil (24), for inductively charging the battery in the pulse generator. The fixture on the antenna for mounting the antenna on the skin of the person is reused for being received in a charger fixture (20) on the charger, containing the primary coil (22) for the transfer of charging power.

24 Claims, 4 Drawing Sheets

SYSTEM FOR ELECTRICAL STIMULATION OF NERVES

TECHNICAL FIELD

The present invention is generally concerned with the art of electrical stimulation of nerves.

BACKGROUND OF THE INVENTION

Electrical stimulation of nerves or its branches is known to be effective in the treatment of a variety of neurological disorders in living beings spanning from treatment of incontinence to gait disorders.

For treating gait disorders, especially correcting drop-foot, electrodes are placed in the proximity of the peroneal nerve or its branches. A pulse generator connected to the electrode generates a pattern of pulses to stimulate the nerve which will cause the foot dorsiflexor muscles to contract. Thus the foot will be lifted and it will be possible for the patient to swing the leg in a more natural manner. An example of a system for correction of drop-foot is known from U.S. Pat. No. 7,403,821 B2 to Neurodan A/S. The document covers the medical aspects and examples of various preferred embodiments are disclosed. For the triggering of the electrical stimulation of the nerve, according to the wanted reaction of the foot, the use of a foot switch is disclosed. Both the heel-off and heel-strike can be detected and used for input to the pulse generator in order to calculate and initiate the appropriate pulse pattern to be fed to the electrode. The foot switch can be connected to the pulse generator with electrical wires or the foot switch can include a wireless transmitter module for communicating the pulse generator. For the interface between the pulse generator and the electrode the system comprises an inductive link, an antenna to be mounted on the skin of the patient and a counterpart in form of an implantable antenna adapted to be implanted in the thigh of the patient. The pulse generator is equipped with a battery, primary or rechargeable, capable of supplying the system with a source of electrical energy. If the battery is rechargeable, the system is equipped with a connector for attaching a power supply.

Of special concern when designing systems to be used by hemiplegic patients suffering from a stroke is that the system should be easy to use and maintain. It should be possible to operate the device with one hand alone. Thus a disadvantage can be seen in that the system features connectors to be plugged in order to assemble the system or recharge the device. Plugging and unplugging connectors can be a challenging task for hemiplegic patients. Another aspect is patient safety, where charging the battery should be prevented when the system is carrying out electrical stimulation of nerves.

There seems to be room for improvements in the design for providing a system that is simpler to use by hemiplegic patients and in addition avoids the situation where charging and electrical stimulation is carried out simultaneously.

DESCRIPTION OF THE INVENTION

It is an object of the present invention to provide a system for stimulation of nerves, which is simpler to use by hemiplegic patients and in addition avoids the situation where charging and electrical stimulation is carried out simultaneously.

In a first aspect, the present invention provides a system for stimulation of nerves comprising at least one electrode, a pulse generator for generating a pulse pattern to be forwarded to that at least one electrode, the pulse generator further being equipped with a rechargeable battery for supplying the system with a source of electrical energy, an inductive link between the pulse generator and the electrode, comprising an antenna adapted to be mounted on the skin of the patient and a counterpart in form of an implantable antenna adapted to be implanted in the thigh of the patient and an inductive link for charging the rechargeable battery in the pulse generator comprising an antenna for acting as a counterpart for an inductive charger where the antennas for the inductive links are arranged in such a way that only one of the inductive links can be in an active coupled connection with its counterpart at a time.

Since the inductive links cannot be actively coupled simultaneously because of the mechanical preventions there will be no risk of inducing power from the charger directly to the implantable electrode.

More detailed, the inductive link for charging the rechargeable battery comprises a first inductive coil forming the primary coil of the charging transformer and a second inductive coil forming the secondary coil of the charging transformer.

The first inductive coil is arranged with a charger device where the charger is intended to be supplied with a source of electrical power as e.g. from a wall outlet. Other alternative supplies could be used as e.g. a USB port from a computer or a battery pack arranged external to the charger device or embedded with the charger device.

The second inductive coil is further connected electrically with the pulse generator. This is achieved with an electrical wire of a length that fits the distance between the patient's hip and thigh.

More specific the second inductive coil is arranged in the housing of the antenna adapted to be mounted on the skin (thigh) of the patient. This arrangement where the antenna for the inductive link between the pulse generator and the electrode and the second inductive coil of the inductive link for charging the battery are both placed in the housing of the antenna provides a system that physically prohibits charging of the battery when the antenna is in a position where the inductive link between the pulse generator and the electrode is assembled and capable of performing electrical stimulation of nerves.

In order to recharge the battery the antenna, with the second inductive coil embedded, has to be removed from the position on the skin (thigh) of the patient and placed in a charging device featuring the first inductive coil. With this arrangement the first and second inductive coils are together forming the inductive link for charging of the battery.

Thus, the first inductive coil is arranged in a holding arrangement adapted for further receiving the second inductive coil and aligning the first and the second inductive coil in position to form a charging transformer.

The holding arrangement will in an appreciated embodiment be arranged in a charger device that also includes the means for connecting the charger to a source of electrical energy as e.g. a wall outlet or other electrical source of energy such as a USB connector or equivalent. The electronics for generating the oscillating current to be fed to the first inductive coil could be included in the charger device. It will be appreciated if the charger is also equipped with control systems for controlling the current flow to the first inductive coil. Especially the control system should include a temperature sensor that regulates down or stops the current flow when the temperature of the antenna is higher than the acceptable level. This arrangement will be able to avoid the dangerous situation where a heated up antenna is removed from the charger and placed on the thigh.

An energy efficient charger device will feature a holding arrangement that keeps the first and second inductive coils in a close and stable position relative to each other during charging. This advantage can be obtained by forming the receiving means for receiving the second inductive coil as a slit or pocket formed as a counterpart for the housing of the antenna. In this way the second inductive coil placed in the housing of the antenna can be guided into the position where it fits the position of the first inductive coil and together forms a transformer for supplying the pulse generator with a supply of electrical energy for charging the battery. It has to be understood that electronic circuits for processing the electrical energy induced into the second inductive coil has to be added for providing an electrical source of energy that is suitable for charging the battery. The electronic circuits can be arranged in the housing of the antenna and/or in the pulse generator.

When carrying out electrical stimulation of nerves, the antenna in its housing is to be mounted on the skin of the patient by the use of a mounting fixture as described in U.S. Pat. No. 7,574,262 B2 to Neurodan A/S which is hereby incorporated by reference. Referring to the part of the mounting fixture that is designed to be arranged on the skin, a similar in shape mounting fixture can be arranged on the charger device for mounting the antenna housing on the charger device. The mounting fixture could be arranged in such a way on the charger device that when the antenna device is fixed in the position where the mounting parts are fixed and locked together, the first inductive coil and the second inductive coil are aligned in position to form a charging transformer. More detailed, this is possible since the antenna housing comprises a cylindrical boss with a flange that forms a mutually working locking mechanism with the hole of the mounting fixture on the charger device. The diameter of the flange is such that the boss cannot pass back through the hole. In other words, the receiving means for receiving the second inductive coil is a mounting fixture adapted to receive a boss carried out on the antenna and keep the boss in a fixed position relative to the mounting fixture. When the antenna housing has to be released from the mounting fixture it has to be slid out of the hole into a larger diameter hole out of which the flange can freely pass.

Rotational movement of the antenna housing relative to the mounting fixture is possible, since the cylindrical boss is free to rotate within the hole of the mounting fixture. In an embodiment the first and second inductive coils are arranged where the center of the coil is the longitudinal centerline of the boss. The magnetic field created by the first inductive coil will then also flow through the second inductive coil and thereby provide a transformation of electrical power. The efficiency will be improved if the boss comprises a soft ferromagnetic material, which is a material showing hysteresis with low coercivity. The boss can be carried out in a soft ferromagnetic material as one piece or be carried out in an isolating material such as plastic and be hollow, where the cavity is filled with a soft ferromagnetic material. For the highest efficiency of the transformer it will be appreciated if the coils are arranged as close as possible to the boss. In a preferred embodiment the first inductive coil is having a soft ferromagnetic core out of which the mounting fixture is formed in at least one end and/or the second inductive coil is having a soft ferromagnetic core that is protruding out into the boss or forming the boss in one end.

In a special embodiment the first and second inductive coils forms a transformer to charge the battery where in addition, the inductive link originally to be used between the pulse generator and the electrode ending up in the antenna, is used for providing a feedback information to the charger from the pulse generator. The charger could in one embodiment include an inductive coil that is capable of recognizing the signal send to the antenna from the pulse generator, but in principle the first inductive coil could be used also for this purpose. Using this interface, it will be possible for the pulse generator to send requests to the charger for setting specific parameters of the charger as e.g. putting the charger in an active or standby mode or e.g. setting the charge current. Especially the possibility of putting the charger in a standby mode after the battery has been fully charged is an appreciated feature that has the overall purpose of saving energy. It has to be secured that no signals are send to the inductive link for the antenna without the antenna being placed in the charging fixture. This can be achieved by only accepting feedback signals to be send when a charging voltage is present since it is then evident that the antenna is placed in the charging fixture. When charging is done the pulse generator simply sends the feedback signal to the charger, and the charger turns off at least for a period of time to be specified. A time of thirty seconds or more seems to be an appropriate time. After the specified standby time expires, the charger starts charging again, but receives immediately the standby feedback signal from the pulse generator and responds with entering the standby mode again for continuing the task until the antenna is removed from the charging fixture. The charger should in a preferred embodiment also be able to check if a second inductive coil is placed in the charging fixture. In case there is an absence of a second inductive coil in the fixture the charger should enter a standby mode. The ability to check the presence of a second inductive coil in the fixture could in a simple embodiment be based on a switch being mechanically activated by the physical presence of the antenna. When an antenna is placed in the fixture charging could be initiated automatically. This design features a charger that can be completely disconnected from the mains when not used as a charger but still being left in the mains socket without any current consumption. In other words, the mechanical switch provides means for checking if a second inductive coil is placed in the charging fixture and on condition that the second inductive coil is placed in the charging fixture connects the charger to a supply and on condition that the second inductive coil is not present disconnect the supply and thus avoids standby power consumption.

If the charger is not featuring a switch as mentioned above it could on a timely basis as e.g. once every minute check the presence of a second inductive coil based on the current drawn from the charger. In this design the charger now and then has to enter a wake up mode for checking if a second inductive coil is placed in the charger fixture, which would incur if not a continuous standby power consummation then at least a consummation when the measurement is going on. However, this standby current might be very low.

The invention is not limited to the physical embodiment of the device as shown in the drawing. The physical size and shape of the pulse generator shown in the drawing is designed with the background of a need for an easy user operation of the device with control buttons and a need for a large battery. An appreciated embodiment will be a slim integrated housing that includes both the pulse generator and the antenna together with the connection cable. The brick like device can in an easy operation be arranged on the thigh e.g. by the use of a fixture as described earlier. Thus the same applies also for this embodiment that the pulse generator can be in a first position (on the human body) where the inductive link between the pulse generator and the electrode is active coupled and where the inductive link for charging the rechargeable battery in the pulse generator is in an inactive coupled state and where the pulse generator in a second position can be placed in a holding arrangement on a charger where the inductive link for charging the rechargeable battery in the pulse generator is active coupled and the inductive link between the pulse generator and the electrode is in an inactive coupled state such that no energy flow in the inductive link between the pulse generator and the electrode during charging of the battery in the pulse generator. More specifically this can be achieved by activating the charger by a switch arranged in the charger device in such a way that it can only be activated when the pulse generator device or at least the antenna of the device is placed in the receptacle of the charger in which position the antennas of the inductive link between the pulse generator and the electrode cannot be in the proximity where they can be in an active coupled state for inductively transferring energy.

Easy handling of the device is achieved by the simple design of the device that might be carried out without connectors that has to or can be plugged or unplugged. The pulse generator is placed in a fixture specially adapted for receiving the pulse generator, typically placed on the hip, and the antenna is placed in the mounting fixture on the thigh and the system can be used for stimulation of nerves. When the system is not used for electrical stimulation of nerves as e.g. when the person rests in bed during the night, the system is placed hanging on the charger device with the antenna placed in the charger fixture. When the system is needed again, it is easy for the patient (with one single hand) to remove it from the charger and place it on the body. Thus the device appears very user friendly, adapted to be used by hemiplegic patients.

DESCRIPTION OF THE DRAWING

Embodiments of the invention will be described with reference to the accompanying drawing, in which.

Figure 1:
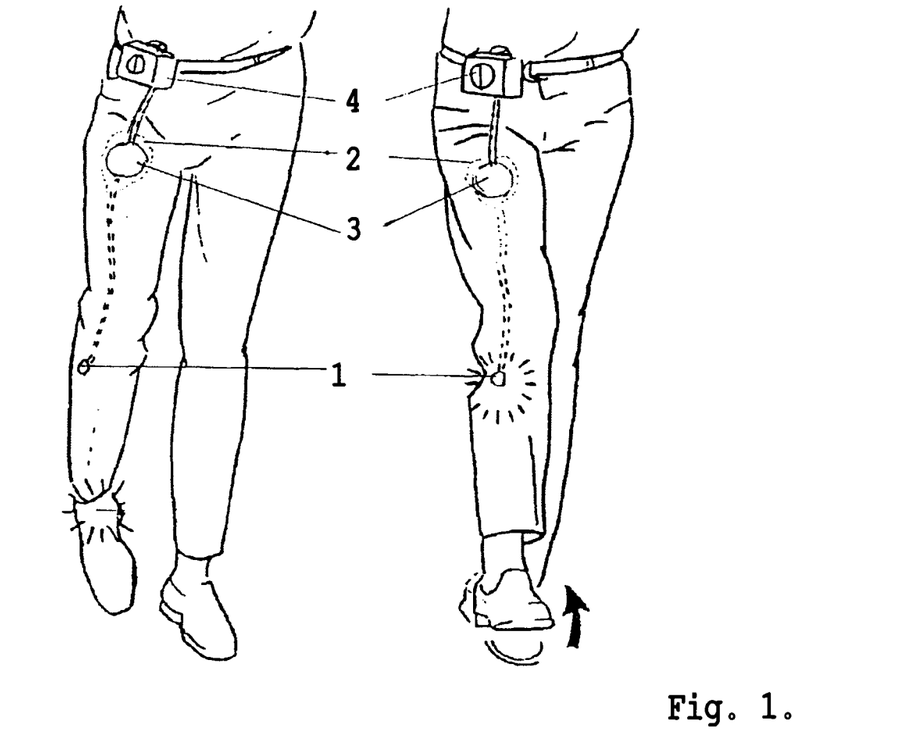
FIG. 1, shows an illustration of a leg region of a patient including a pulse generator with antenna and implant with lead and electrode.
Figure 2:
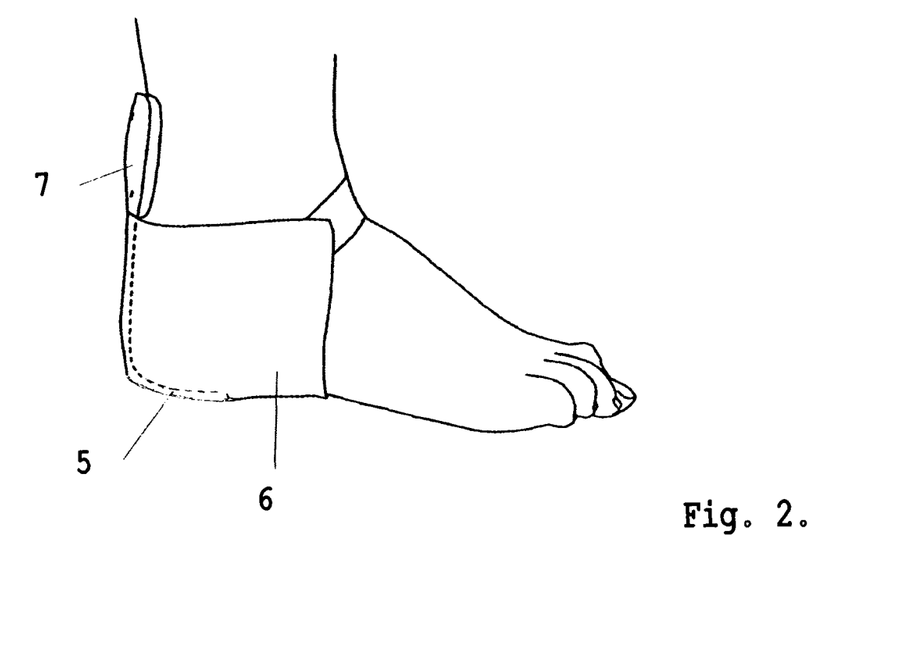
FIG. 2, shows an illustration of a foot with a sock for fixation of a heel switch.

The system for electric stimulation of nerves shown in the drawing includes an implanted electrode 1 electrically connected to an implanted module 2. On the skin of the human body in the proximity of the implanted module 2 is placed an antenna 3, the antenna 3 being connected to the pulse generator 4. Thus the pulse generator 4 supplies signals for inductively powering the implanted module 2 and providing pulses of electrical current to the implanted electrode 1. The electrode 1 is a CUFF electrode, a tubelike isolating fixture with a number of electrodes the fixture fully embracing the nerve to be stimulated at least over a distance of the length of the nerve. The specific nerve to be stimulated in the present application is the Peroneal nerve. Stimulating the nerve has the effect to cause the foot dorsiflexor muscles to contract. Thus the foot will be lifted and a more natural swing phase of the gait can be achieved. The stimulation signal must be synchronized with the gait of the patient, thus the need for a trigger that reflects a well defined event of the foot. The heel-strike and heel-off events are useful events for determining the gait cycle of the patient and can easily be obtained using a foot switch. To avoid wiring between the controller and the foot switch a wireless communication link is used. An example of a state of art foot switch 5 is shown in FIG. 2. The foot switch device is fixed to the foot with the use of a sock 6. Normally the trigger is equipped with a transmitter 7 and the pulse generator 4 is equipped with a receiver.

Figures 3, 5, 6, 7:
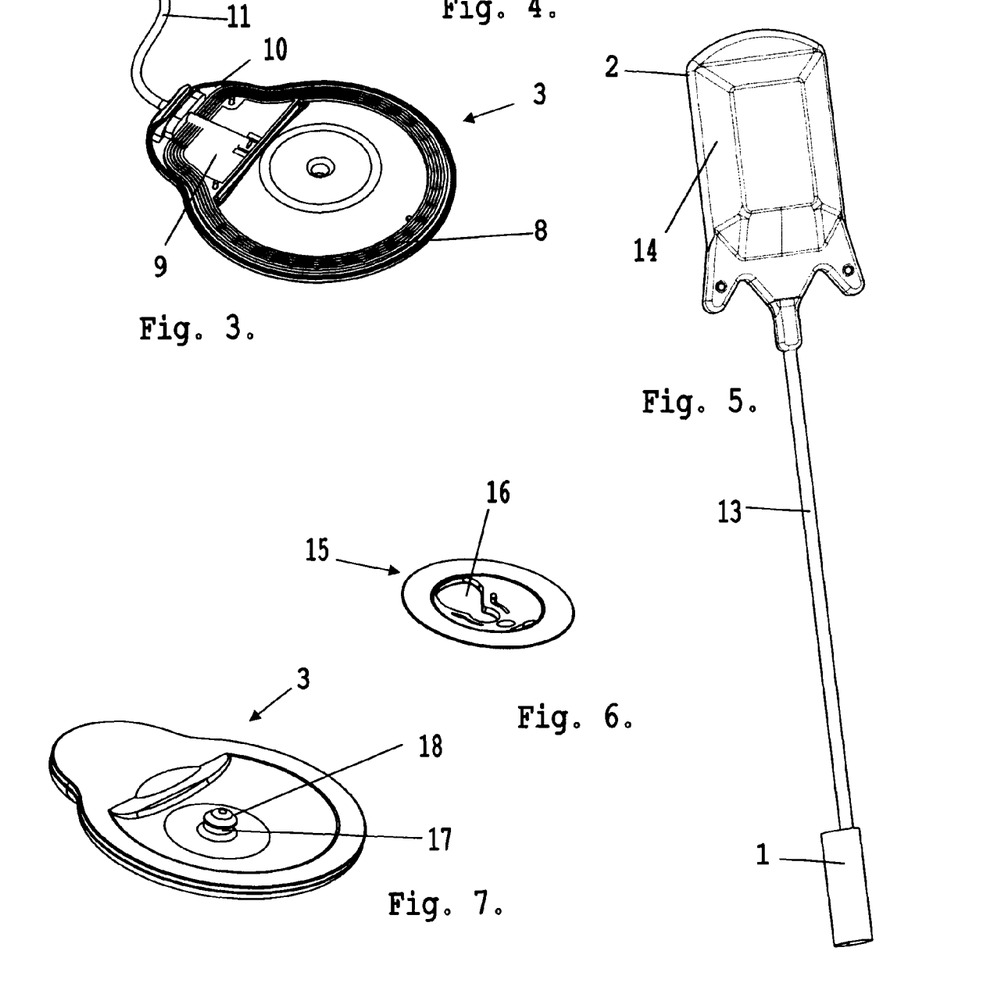
FIG. 3, shows a detail of the antenna for the inductive link between the pulse generator and the implant.
FIG. 5, shows an illustration of the implant consisting of a stimulation body, a lead wire and an electrode.
FIG. 6, shows an illustration of the mounting fixture for mounting the antenna on the thigh of the patient.
FIG. 7, shows an illustration of the antenna with a mounting boss for mounting the antenna in a mounting fixture.
Figure 4:
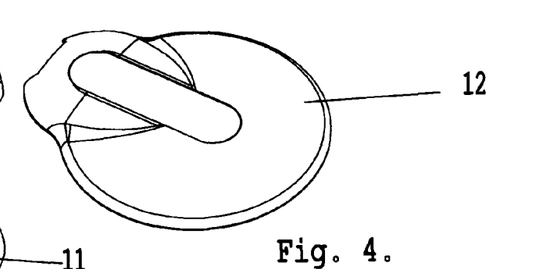
FIG. 4, shows a lid that is a part of the housing for the antenna.

The inductive link between the pulse generator 4 and the electrode 1 is consisting of an antenna 3 adapted to be mounted on the skin of the patient and a counterpart in form of an implantable module 2 adapted to be implanted in the thigh of the patient. The antenna coils 8 are carried out on a printed circuit board 9 fixed in a first housing part 10 adapted for receiving a wire 11 that connects the antenna 3 with the pulse generator 4. A lid substituting a second housing part 12 for protecting the antenna 3 and closing the housing 10 of the antenna is shown in FIG. 4. For explanation of the system FIG. 5 shows the implantable part of the system consisting of a implantable module 2, a lead wire 13 and an electrode 1. The implantable module 2 includes an antenna 14 that serves as an implanted counterpart to the antenna 3 adapted to be mounted on the thigh of the patient. Using the inductive link, the signal generated by the pulse generator 4 is transferred inductively from the antenna 3 on the thigh to the antenna 14 implanted in the thigh and fed via the lead wire 13 to the electrode 1. The electrode 1 is in the preferred embodiment a CUFF electrode, a type of electrode where the contacts in the electrode is placed on a silastic sheet that can be wrapped around the nerve to be electrically stimulated.

For mounting the antenna 3 on the thigh of the patient, a mounting fixture 15 as shown in FIG. 6 is used. The mounting fixture 15 includes an adhesive foil that can be used for attaching the fixture 15 on the skin of the patient. The mounting fixture 15 features an oval hole 16 for mounting the antenna 3 in a fixed position. A detail of the antenna 3, showing the first housing part 10 of the antenna with a view to the side adapted to be facing the skin of the patient, is shown in FIG. 7. The boss 17 is adapted to fit the hole 16 in the mounting fixture 15 in a way where the two parts 3, 15 form mutually locking mechanisms for keeping the two parts in a fixed position in relation to each other. More specific the oval hole 16 in the mounting fixture 15 has a dimension that allows the flange 18 of the boss 17 to pass through the hole 16 in one position, but in another position of the hole 16 has a dimension that is adapted to avoid the boss 17 to be drawn out of the hole 16 again. In this way the boss 17 is kept in a fixed position in the hole 16.

Figure 8:
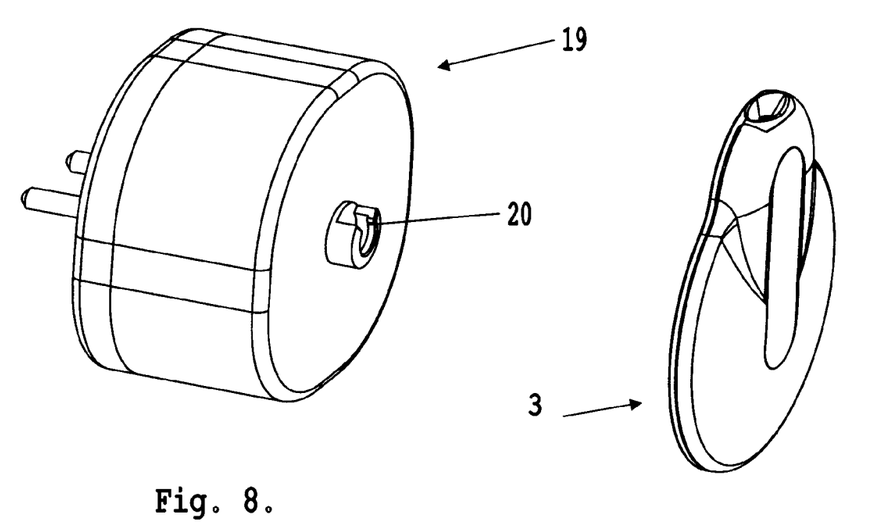
FIG. 8, shows an embodiment of a charger device with a mounting fixture for receiving the antenna.

A charger 19 according to the invention is carried out as shown in FIG. 8, where the charger is adapted to be mounted directly in a electric power wall outlet. The charger is designed as an inductive charger where a primary inductive coil is kept with the charger and the secondary inductive coil is placed at the consumer. As can be seen from FIG. 8, the charger includes a part, hereby called a charger fixture 20 that are carried out having similar facilities for receiving the boss 17 as a mounting fixture, adapted to receive the boss 17 of the antenna 3 and keep the boss 17 in a fixed position. The charger fixture 20 is carried out in a soft ferromagnetic material that also forms the core 21 for the primary inductive coil 22. Since the boss 17 is having a core 23 made fully or partly of a soft ferromagnetic material the magnetic field runs through both the core 21 of the primary inductive coil 22 in the charger 19 and the core 23 of the secondary inductive coil 24 in the antenna 3. Therefore, it will be possible to induce an electric current in the secondary inductive coil 24. More detailed, the boss 17 is in this embodiment made hollow and the secondary coil 24 and the soft ferromagnetic core 23 is arranged in the cavity. Especially appreciated is a hollow boss 17, where the boss 17 is made of an electrical isolating material as e.g. a plastic, since with this design there is low risk of leakage currents from the pulse generator 4 to the skin of the patient. Anyhow a solution with a boss 17 made completely of soft ferromagnetic material as e.g. a ferrite metal could possibly be used where the charger fixture 20 comprises the necessary means for isolation towards the skin of the patient.

Figure 9:
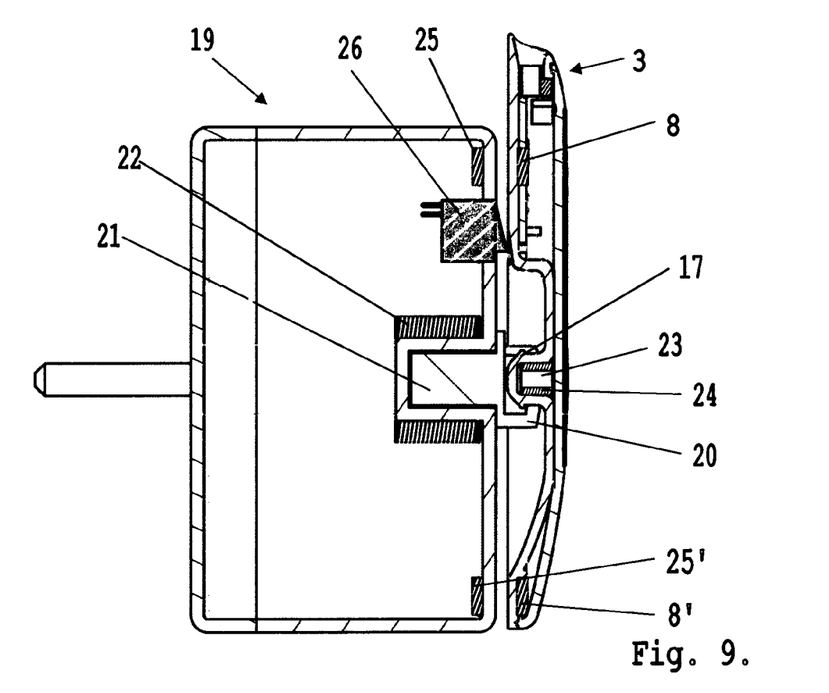
FIG. 9, shows a cross section of the charger device with an antenna attached.

Another feature of the invention is shown in FIG. 9, where the antenna is using the coil 8 of the inductive link, the coil to be used towards the implant, for another purpose, namely communication with the inductive charger 19. The charger 19 is equipped with a further coil 25 intended for receiving feedback information from the pulse generator 4 on the state of charging. Using this interface, it will be possible for the pulse generator 4 to send requests to the charger for setting specific parameters of the charger as e.g. putting the charger in an active or standby mode or e.g. setting the charge current. Especially the possibility of putting the charger in a standby mode after the battery has been fully charged is an appreciated feature that saves energy. It has to be secured that no signals are send to the inductive link for the antenna 3 without the antenna 3 being placed in the charging fixture 20. This can be achieved by only accepting feedback signals to be send when a charging voltage is present since it is then evident that the antenna 3 is placed in the charging fixture 20. When charging is done the pulse generator 4 simply sends the feedback signal to the charger 19, and the charger goes into a standby mode at least for a period of time to be specified. A time of 30 seconds or more seems to be an appropriate time. After the specified standby time expires, the charger 19 starts charging again, but receives immediately the standby feedback signal from the pulse generator 4 and responds with entering the standby mode again for continuing the task until the antenna is removed from the charging fixture 20. Further the charger comprises a switch 26 for determining if an antenna 3 is placed in the charger fixture 20. The switch 26 breaks the supply to the charger 19 completely when no antenna 3 is fixed. In one embodiment the switch directly cuts the 230 Volt supply. In another embodiment, featuring a capacitor working as a storage of electrical energy, the switch use the electrical charge on the capacitor to initiate an electronic switch for switching on the supply from the mains. The charge on the capacitor is maintained and can be used next time a charging session is started. A capacitor with a low leak current is preferred since if discharged it might not be possible to switch on the charger. This problem can be solved by adding a push button that can be pushed to initiate charging. A better solution is to make a charge transfer to the capacitor every time the device is plugged in an active wall outlet. Thus it is possible to leave the charger 19 in the wall outlet without any standby power consumption.

Figure 10:
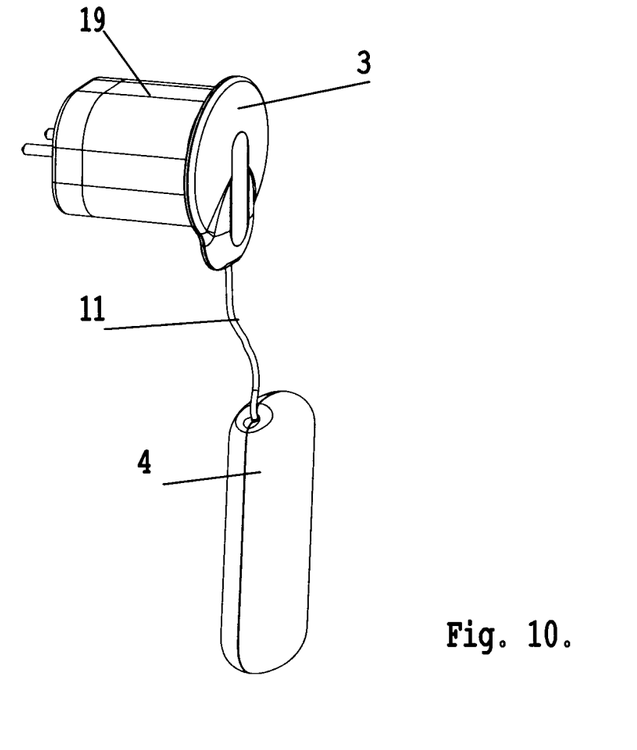
FIG. 10, shows an illustration of the charger device with an antenna attached and the pulse generator hanging in a wire

FIG. 10 shows a typical use of the charger 19, where the antenna 3 is placed in the charger fixture 20. The pulse generator 4 is in this embodiment connected to the antenna 3 with a fixed cord 11. The device 3, 11, 4 is simpler to use by hemiplegic patients since it can be handled with one single hand. Additionally the charger 19 serves as a place to put the external part of the system, the antenna 3 and pulse generator 4, when not in use. It is easy to grab and mount on the thigh from this place. It is easy to detach from the thigh and put on the storing place, and additionally the rechargeable battery in the pulse generator 4 will be recharged when the device is not in use. There are no additional cords or parts that have to be used apart from the charger 19, which makes a very user friendly and simple product to use in the daily life of a patient suffering from drop-foot.

Figure 11:
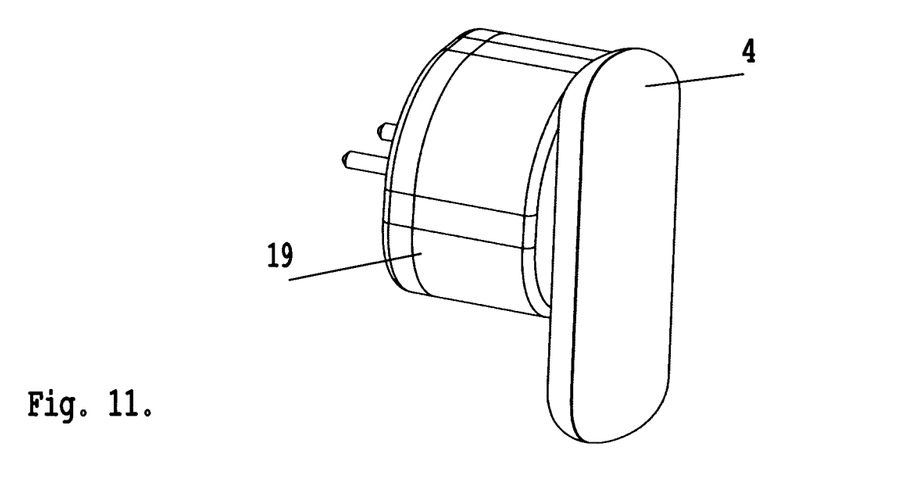
FIG. 11, shows an illustration of the charger device with a device attached in which the pulse generator and antenna is arranged together in one cabinet.

FIG. 11 shows an appreciated embodiment of the device where the pulse generator and the antenna for the inductive links are arranged together in one cabinet. The cabinet is equipped with the fixture for mounting the antenna on the counterpart to be placed on the thigh or at the receiving part of the charger. Since the antenna is centered on the boss of the fixture the function of the inductive link is independent on the angular placement of the device in relation to the charger or on the thigh in active connection with the implantable counterpart just as in the case with the cable connected antenna device. This embodiment is appreciated since it provides a slim device that is easy to handle and easy to hide behind the clothing which renders it more social accepted. It could be equipped with control buttons and indicators or be controlled by remote control.

However, it will be appreciated if the invention is not limited to systems for correction of drop-foot, but also cover neurostimulation systems for other purposes having the characteristics of featuring an inductive link between an external pulse generator 4 and an implantable system where the antenna 3 to be placed outside the body in addition features a coil 24 for receiving an inductive charge.

For the sake of simplicity of this application, details of oscillating frequency of the inductive charger and physical size of the coils are not explained since the person skilled in the art will still be able to use the instructions for carrying out the invention.

The invention claimed is:

1. A system for electrical stimulation of a peroneal nerve in a thigh of a patient, comprising:
   at least one electrode configured to contact the peroneal nerve,
   a pulse generator for generating a pulse pattern to be forwarded to the at least one electrode, the pulse generator being equipped with a rechargeable battery for supplying the system with a source of electrical energy,
   a first inductive link between the pulse generator and the electrode, and comprising an antenna adapted to be mounted on the skin of the patient and configured to communicate with a counterpart in form of an implantable module having an antenna and adapted to be implanted in the thigh of the patient,
   an inductive charger having a first mounting feature,
   a second inductive link for charging the rechargeable battery in the pulse generator comprising an antenna configured to be a counterpart for the inductive charger,
   a single housing provided separate from the pulse generator,
   a mounting fixture operable to connect the single housing to the skin of the patient, the mounting fixture having a second mounting feature,
   a connecting boss protruding from a surface of the single housing and configured to extend into and releasable connect with either one of the first and second mounting features,
   wherein the antennas for the first and second inductive links are arranged in the single housing which is connectable either to the inductive charger or the skin of the patient such that only one of the first and second inductive links can be in an active coupled connection with its counterpart at a time.

2. A system according to claim 1, wherein the second inductive link for charging the rechargeable battery comprises a first inductive coil forming the primary coil of a charging transformer and a second inductive coil forming the secondary coil of the charging transformer.

3. A system according to claim 2, wherein the second inductive coil is arranged in the housing of the antenna adapted to be mounted on the skin of the patient.

4. A system according to claim 2, wherein the first inductive coil is arranged in a holding arrangement adapted for further receiving the second inductive coil and aligning the first and the second inductive coil in position to form a charging transformer.

5. A system according to claim 4, wherein the holding arrangement is embedded in the inductive charger, the inductive charger further including a connecting member configured to connect the inductive charger to a source of electrical energy.

6. A system according to claim 4, wherein a receiving member of the first inductive coil for receiving the second inductive coil is a slit that is formed as a counterpart for the antenna.

7. A system according to claim 2, wherein the first inductive coil comprises a soft ferromagnetic core out of which the mounting feature of the inductive charger is formed in at least one end thereof and/or the second inductive coil comprises a soft ferromagnetic core that is protruding out into the boss or forming the boss in one end of the single housing.

8. A system according to claim 2, wherein the inductive charger further comprises a checking member operable to confirm if the second inductive coil is mounted to the inductive charger.

9. A system according to claim 8, wherein the checking member is a mechanical switch that on condition that the second inductive coil is placed in the charging fixture connects the charger to a supply and on condition that the second inductive coil is not present disconnect the supply and thus avoid standby power consumption.

10. A system according to claim 8, wherein the checking member checks the presence of the second inductive coil based on applying a charge with the inductive charger and a measurement of the current drawn from the inductive charger.

11. A system according to claim 1, wherein the first inductive link, originally to be used between the pulse generator and the electrode ending up in the antenna, provides feedback information to the charger from the pulse generator about the state of charging the battery and/or control commands for putting the charger in an active or standby mode.

12. A system according to claim 1, wherein the pulse generator in a first position is arranged in a position on the human body where the first inductive link between the pulse generator and the electrode is active coupled and where the second inductive link for charging the rechargeable battery in the pulse generator is in an inactive coupled state and a second position where the pulse generator is arranged in a holding arrangement on a charger where the second inductive link for charging the rechargeable battery in the pulse generator is active coupled and the first inductive link between the pulse generator and the electrode is in an inactive coupled state such that no energy flow in the first inductive link between the pulse generator and the electrode during charging of the battery in the pulse generator.

13. A system according to claim 1, wherein the inductive charger further comprises a switch that is arranged in such a way in the inductive charger device that the switch can only be activated when the pulse generator device or at least the single housing placed in the mounting feature of the inductive charger in which position the antennas of the first inductive link between the pulse generator and the electrode cannot be in the proximity where they can be in an active coupled state for inductively transferring energy.

14. A system according to claim 1, wherein the pulse generator is configured to be operated by a wireless remote control.

15. A system according to claim 1, wherein the single housing is rotatable about the connecting boss when mounted to either one of the inductive charger and the mounting fixture used to connect the single housing to the skin of the patient.

16. A system according to claim 1, wherein the antennas are arranged coaxially in the single housing.

17. A system according to claim 1, further comprising a temperature sensor operable to monitor a temperature of at least one of the single housing and the antennas.

18. A system according to claim 1, wherein the connecting boss is arranged coaxially with the antennas that are positioned in the single housing.

19. A system according to claim 1, wherein at least one of the antenna of the first inductive link and the antenna of the second inductive link is arranged coaxially with the connecting boss.

20. A system for electrical stimulation of a peroneal nerve in a thigh of a patient, comprising:
   at least one electrode configured to contact the peroneal nerve;
   a module configured to be implanted in the thigh of a patient;
   an inductive charger;
   a pulse generator configured to generate a pulse pattern to be forwarded to that at least one electrode, the pulse generator having a rechargeable battery;
   a first inductive link operable between the pulse generator and the electrode, the first inductive link including a first antenna, being configured to be mounted on skin of the patient, and being configured to communicate with the module through the skin of the patient;
   a second inductive link including a second antenna and being operable between the pulse generator and the inductive charger to charge the rechargeable battery;
   a mounting fixture configured to be mounted to the skin of the patient;
   a housing provided separate from the pulse generator, the first and second antennas being arranged in the housing, the housing being connectable either to the inductive charger or the mounting fixture such that only one of the first and second inductive links is in an active coupled connection with either the module or the inductive charger, respectively, at a time;
   a connecting boss protruding from a surface of the housing and configured to extend into and releasably connect with a mounting feature of either one of the inductive charger and the mounting fixture, at least one of the first and second antennas being arranged coaxially with the connecting boss.

21. A system according to claim 20, wherein the inductive link for charging the rechargeable battery comprises a first inductive coil forming a primary coil of a charging transformer and a second inductive coil forming a secondary coil of the charging transformer.

22. A system according to claim 21, wherein the second inductive coil is arranged in the housing.

23. A system according to claim 21, wherein the first inductive coil is arranged in a holding arrangement adapted for further receiving the second inductive coil and aligning the first and second inductive coils in position to form a charging transformer.

24. A system according to claim 23, wherein the holding arrangement is embedded in the inductive charger, the inductive charger being configured to connect the inductive charger to a source of electrical energy.

* * * * *